United States Patent [19]
Tanaka et al.

[11] Patent Number: 6,048,890
[45] Date of Patent: Apr. 11, 2000

[54] PHENYLAMIDINOTHIOPHENE DERIVATIVES AND ANTI-INFLAMMATORY AGENT CONTAINING THE SAME

[75] Inventors: Kiyomi Tanaka; Tokiko Nishida; Jun Nakano; Mamoru Inoue; Tsutomu Nakamura, all of Kyoto; Hayami Debuchi, Sapporo, all of Japan

[73] Assignee: Kaken Pharmaceutical Co., Ltd., Tokyo, Japan

[21] Appl. No.: 08/894,627

[22] PCT Filed: Feb. 19, 1996

[86] PCT No.: PCT/JP96/00372

§ 371 Date: Dec. 1, 1997

§ 102(e) Date: Dec. 1, 1997

[87] PCT Pub. No.: WO96/26204

PCT Pub. Date: Aug. 29, 1996

[30] Foreign Application Priority Data

Feb. 24, 1995 [JP] Japan .................................. 7-037043

[51] Int. Cl.[7] .......................... A01N 43/06; C07D 333/00
[52] U.S. Cl. .............................. 514/438; 549/74; 549/75; 549/78
[58] Field of Search ................................ 514/438; 549/75

[56] References Cited

U.S. PATENT DOCUMENTS 4,066,670  1/1978  Pelosi, Jr. et al. .................... 260/347.7
4,302,461  11/1981  Cherkofsky ............................ 424/263

FOREIGN PATENT DOCUMENTS

WO 91/19708  12/1991  Japan .

*Primary Examiner*—Dwayne C. Jones
*Attorney, Agent, or Firm*—Sughrue, Mion, Zinn, Macpeak & Seas, PLLC

[57] ABSTRACT

A thiophene derivative containing a phenylamidino group represented by the general formula (I):

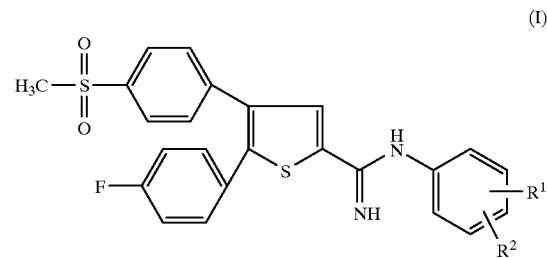

wherein $R^1$ and $R^2$ are the same or different from each other and are hydrogen atom, a halogen atom, an alkyl group having 1 to 4 carbon atoms or an alkoxyl group having 1 to 4 carbon atoms; or a pharmacologically acceptable salt thereof. The compound is useful for the treatment of inflammatory diseases.

5 Claims, No Drawings

PHENYLAMIDINOTHIOPHENE DERIVATIVES AND ANTI-INFLAMMATORY AGENT CONTAINING THE SAME

This application is a 371 of PCT/JP96/00372 filed on Feb. 19, 1996.

TECHNICAL FIELD

The present invention relates to novel phenylamidinothiophene derivatives and salts thereof showing an anti-inflammatory action without causing the lesion of digestive organs, and an anti-inflammatory agent containing the same.

More particularly, the present invention relates to novel phenylamidinothiophene derivatives possessing an anti-inflammatory action, and medicaments containing these derivatives as an effective ingredient for the prevention and/or treatment of various inflammation reactions, and collagen disease, autoimmune disease and other various immune diseases in human being or animals.

BACKGROUND ART

Most of medicaments having an amidino group are circulatory agents, and others thereof are anti-histamic agents and few thereof are central nervous system-acting agents (Progress in Medicinal Chemistry, Vol. 30, pages 203 to 326, 1993, published by ELSEVIER CO., LTD.). As an anti-inflammatory agent, there are only naphazoline (for rhinitis) and the like (Progress in Medicinal Chemistry, Vol. 30, page 257, 1993, published by ELSEVIER CO., LTD.). However, all of the chemical structures of these agents are those having an amidino group at the end of the molecule and not those having an amidino structure intermediate between a thiophene ring and a phenyl ring as proposed by us in this invention. With respect to medicaments having a thiophene ring, those having anti-inflammatory action are disclosed, for example, in JP,B,3-14312 and International Publication WO 91/19708 (Tokuhyo-Hei 6-501919). However, none of them have an amidino group. Thus, the compounds proposed by us have a structure containing a phenylamidino group, which structure is entirely different from those of conventionally disclosed anti-inflammatory agents.

With respect to pharmacological action of anti-inflammatory agents, it is recognized that non-steroid anti-inflammatory agents clinically widely used, such as aspirin and indomethacin, exert anti-inflammatory action through inhibition of the activity of cyclooxygenase (synthetase of prostaglandin G/H) which is a rate-determining enzyme of prostaglandin production. However, cyclooxygenase exists not only in inflamed regions but also in various tissues and it is recognized that the inhibition of cyclooxygenase activity relates to side effects of non-steroid anti-inflammatory agents on digestive organs or kidney. Lesion of digestive organs among the side effects is a significant factor in limited clinical applications of non-steroid anti-inflammatory agents.

It is an object of the present invention to provide a novel and useful phenylamidinothiophene derivative and a salt thereof showing an anti-inflammatory action without causing lesion of digestive organs.

Another object of the present invention is to provide a medicament containing the phenylamidinothiophene derivative or a pharmacologically acceptable salt thereof as an effective ingredient for the prevention and/or treatment of inflammatory diseases and other diseases mentioned above without causing lesion of digestive organs.

DISCLOSURE OF THE INVENTION

The present inventors have synthesized novel compounds to solve the above-mentioned problems and found phenylamidinothiophene derivatives represented by the general formula (I) mentioned below or their pharmacologically acceptable salts which show inhibitory action on rat adjuvant arthritis and cause little lesion of digestive organs.

The present invention provides a thiophene derivative containing a phenylamidino group represented by the general formula (I):

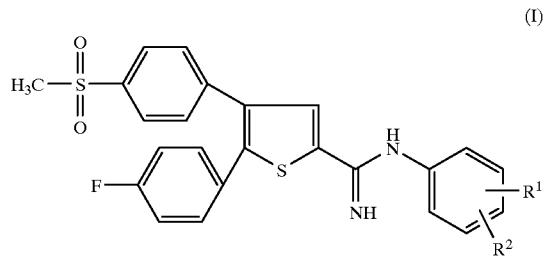

wherein $R^1$ and $R^2$ are the same or different from each other and are hydrogen atom, a halogen atom, an alkyl group having 1 to 4 carbon atoms or an alkoxyl group having 1 to 4 carbon atoms; or a pharmacologically acceptable salt thereof.

The present invention provides the thiophene derivative containing a phenylamidino group or a pharmacologically acceptable salt thereof wherein $R^1$ and $R^2$ in the general formula (I) are the same or different from each other and are hydrogen atom, fluorine atom, chlorine atom, bromine atom, methyl group or methoxy group.

The present invention provides 5-[$N^1$-(3-chlorophenyl)aminido]-2-(4-fluorophenyl)-3-(4-methylsulfonylphenyl)thiophene or a pharmacologically acceptable salt thereof.

The present invention further provides an anti-inflammatory agent containing a thiophene derivative containing a phenylamidino group mentioned above or a pharmacologically acceptable salt thereof.

The present invention still further provides use of a thiophene derivative containing a phenylamidino group mentioned above or a pharmacologically acceptable salt thereof for the prevention and/or treatment of an inflammatory disease.

Examples of the halogen atom represented by $R^1$ and $R^2$ in the general formula (I) are fluorine atom, chlorine atom, bromine atom and iodine atom, among which fluorine atom, chlorine atom and bromine atom are preferred and chlorine atom is especially preferred. Examples of the alkyl group having 1 to 4 carbon atoms are methyl group, ethyl group, n-propyl group, iso-propyl group, n-butyl group and tert-butyl group. Methyl group is especially preferred. Examples of the alkoxyl group having 1 to 4 carbon atoms are methoxy group, ethoxy group, n-propoxy group, iso-propoxy group, n-butoxy group and tert-butoxy group. Methoxy group is especially preferred.

Combinations of kinds and positions of the substituents represented by $R^1$ and $R^2$ in the phenyl group contained in the phenylamidino group are appropriately selected. From the viewpoint of superior anti-inflammatory activity and easy production, preferred are the combinations of kinds and positions of the substituents shown in Table 1, wherein the figures before the substituents indicate their positions.

TABLE 1

| $R^1$ | $R^2$ |
| --- | --- |
| H | H |
| 3-Halogen | H |
| 2-Halogen | H |
| 4-Halogen | H |
| 3-Alkyl | H |
| 4-Alkyl | H |
| 3-Alkoxy | H |
| 4-Alkoxy | H |
| 2-Halogen | 4-Halogen |
| 3-Halogen | 4-Halogen |
| 3-Alkyl | 4-Alkyl |
| 3-Alkoxy | 5-Alkoxy |
| 3-Halogen | 4-Alkyl |

From the viewpoint of superior anti-inflammatory activity and less side effect, the most preferred are 5-[$N^1$-(3-chlorophenyl)amidino]-2-(4-fluorophenyl)-3-(4-methylsulfonylphenyl)thiophene and its pharmacologically acceptable salts.

The compound of the present invention includes pharmacologically acceptable salts of the compounds represented by the general formula (I). Generally the compounds represented by the general formula (I) are basic and, hence, can form pharmacologically acceptable salts by reaction with many nontoxic inorganic or organic acids.

Acids usually used for formation of acid addition salts include inorganic acids such as hydrochloric acid, hydrobromic acid, hydroiodic acid, sulfuric acid and phosphoric acid, organic acids such as p-toluenesulfonic acid, methanesulfonic acid, oxalic acid, succinic acid, citric acid, benzoic acid and acetic acid, and the like. Among those, preferable pharmacologically acceptable acid addition salts are inorganic salts with hydrochloric acid or hydrobromic acid, and organic salts with maleic acid or oxalic acid.

The novel phenylamidinothiophene derivative represented by the general formula (I) in accordance with the present invention can be produced as shown in the following reaction formula (A):

Reaction formula (A)

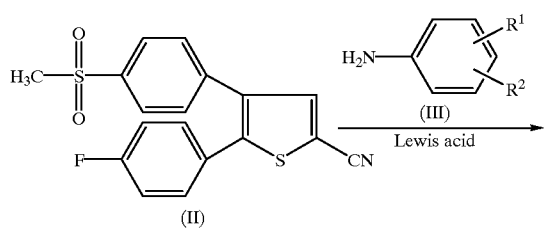

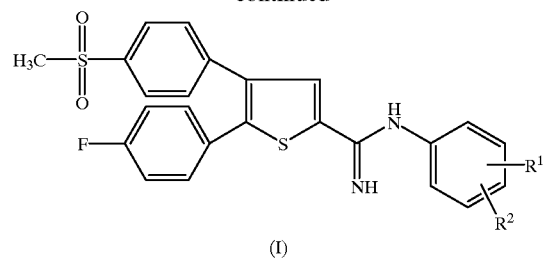

(I)

In reaction formula (A), $R^1$ and $R^2$ are the same as defined above.

According to reaction formula (A), the phenylamidinothiophene derivative (I) can be produced by allowing a compound represented by the general formula (III) to react with 5-cyano-2-(4-fluorophenyl)-3-(4-methylsulfonylphenyl)thiophene (II) [described in International Publication WO 91/19708 (Tokuhyo-Hei 6-501919)] in the presence of a Lewis acid in an appropriate organic solvent.

The organic solvent used in the reaction of compound (II) with the compound represented by the general formula (III) is not particularly limited so long as the solvent does not markedly inhibit the instant reaction. However, preferred are 1,1,2,2-tetrachloroethane, N,N-dimethylformamide, dimethyl sulfoxide, and the like. As the Lewis acid, there are used aluminum chloride, boron trifluoride, tin chloride, zinc chloride, iron chloride, and the like. Aluminum chloride is especially preferred.

With respect to the amounts of respective components in the instant reaction, the equivalent of aniline derivative (III) and that of Lewis acid are preferably 1 to 4 times, more preferably 1.5 to 3 times and preferably 1 to 3 times, more preferably about 2 times, respectively, that of 5-cyano-2-(4-fluorophenyl)-3-(4-methylsulfonylphenyl)thiophene (II). The temperature of the instant reaction is preferably from 25° to 140° C., especially from 80° to 120° C. The reaction time is preferably from 1 to 10 hours, especially from 6 to 9 hours. The treatment after the reaction can be performed by usual treating methods, for example, by isolating and purifying the desired compound by means of a recrystallization method, a chromatography, or the like.

The compound (I) of the present invention and the pharmacologically acceptable salt thereof show an anti-inflammatory action without causing lesion of digestive organs. That is, they possess an anti-inflammatory activity and, moreover, do not inhibit the activity of cyclooxygenase in vitro test, which is different from conventional non-steroid anti-inflammatory agents. Furthermore, they do not show an action of exacerbating lesion of digestive organ in vivo test.

Therefore, the instant compounds are useful as agents for the prevention and/or treatment of various inflammation reactions, and collagen diseases, autoimmune disease and other various immune diseases in human being or animals.

More specifically, the instant compounds are useful as agents for the prevention and/or treatment of inflammation and pain in joints and muscles (e.g. rheumatoid arthritis, rheumatic spinal inflammation, osteoarthritis and gouty arthritis); inflammation of skin (e.g. solar dermatitis), inflammation of eye (e.g. conjunctivitis); symptomatic therapy of inflammatory diseases in external part and fore part of eye (e.g. blepharitis, keratitis, scleritis, ureitis in fore part and postoperative inflammation); prevention of postoperative inflammation and intraoperative or postoperative complication in operation for cataract; lung disease in which inflammation participates (e.g. asthma and bronchitis); digestive organ disease with inflammation (e.g. aphthous ulcer, Crohn's disease, atrophic gastritis, osterogastritis, ulcerative colitis, fatty diarrhea in child, localized iletis and irritable colon syndrome); gingivitis; pain in treatment of carious tooth; headache; pain in menstrual period; inflammation after operation or injury; pain and swelling; pyrexia due to inflammation; and other diseases. Further, the instant compounds are expected to be useful as agents for the prevention and/or treatment of diseases of circulatory organ system or cerebrovascular diseases.

The compound (I) of the present invention or pharmacologically acceptable salt thereof can be administered orally, parenterally or by external application (local application) for the purpose of the above-mentioned prevention and/or treatment.

As the formulations for medicaments, there are capsules, tablets, sugar coated tablets, granules, inhalations, suppositories, liquids, lotions, suspensions, emulsions, ointments, cataplasms, gels, and the like.

As required, these formulations can be incorporated with excipients in organic or inorganic solid or liquid state, auxiliary materials, stabilizing agents, wetting agents, emulsifiers, buffers, or other various additives.

For achievement of the desired therapeutic or preventive effect, the daily dosage of the active ingredient is from 0.01 to 50 mg per kg body weight for human being. Each unit dosage form can contain 1 to 500 mg of the active ingredient in a state that it is mixed with a suitable carrier for medicament. This unit dosage form can be administered 1 to 4 times per day.

BEST MODE FOR CARRYING OUT THE INVENTION

The action and effect of the instant compounds are explained by means of Experimental Examples.

The respective actions of the instant compounds on adjuvant arthritis in rats, stress ulcer in mice induced by constraint under water immersion and the activity of cyclooxygenase of sheep seminal vesicle gland were examined. The test methods and results thereof are shown below.

Experimental Example 1
Action on Rat Adjuvant Arthritis
Test Method

Seven-week old male Lewis rats (4 rats in one group) were injected under the plantar skin of the right hind paw with 0.6 mg/0.1 ml of a suspension of human tubercle bacillus, killed Mycobacterium tuberculosis H37 RA in liquid paraffin, thereby inducing adjuvant arthritis. The volume of the adjuvant-inoculated paw (primary inflammation) was measured 3 days after the inoculation of adjuvant and the volume of the adjuvant-uninoculated paw (secondary inflammation) 17 days after the inoculation of adjuvant. The swelling rate of each paw was calculated with respect to the volume of the paw before the inoculation of adjuvant. Ten mg of the instant compound was suspended in 10 ml of a 0.5% by weight aqueous solution of carboxymethyl cellulose and the oral administration of the obtained suspension began on day of adjuvant inoculating and continued for 17 days in a dose of 10 mg/kg one time per day. Indomethacin was used in a dose of 1 mg/kg as a comparative drug.

Test Results

The test results are shown in Table 2 in terms of inhibition rate obtained as compared with the swelling rate of the paw in the group given 0.5% by weight carboxymethyl cellulose solution. The swelling rate and inhibition rate were calculated according to the following formulae:

$$\text{Swelling rate (\%)} = [(\text{Paw volume at each measuring time} / \text{Paw volume immediately before the adjuvant inoculation}) - 1] \times 100$$

$$\text{Inhibition rate (\%)} = [1 - (\text{Swelling rate of the test compound given rat} / \text{Average swelling rate of the group given 0.5 \% by weight carboxymethylcellulose aqueous solution})] \times 100$$

Each value is an average value for 4 rats in one group and the value in parentheses is standard error.

While in the group given indomethacin 1 mg/kg a swelling inhibition of 28.8% was found for the inoculated paw and a swelling inhibition of 43.6% for the uninoculated paw, there were found inhibitory actions equal to or better than the above values in the groups given the instant compound 10 mg/kg, especially a swelling inhibition of 31.5% for the inoculated paw and a swelling inhibition of 48.9% for uninoculated paw with use of the compound obtained in Example 1.

TABLE 2

| Test compound | Swelling inhibition (%) | |
|---|---|---|
| (Example No.) | Primary inflammation (inoculated paw) | Secondary inflammation (uninoculated paw) |
| 1 | 31.5 (0.91) | 48.9 (3.58) |
| 2 | 22.6 (5.24) | 28.4 (2.55) |
| 3 | 22.1 (4.94) | 32.2 (10.8) |
| 4 | 32.7 (7.40) | 57.4 (8.54) |
| 5 | 23.5 (4.75) | 34.7 (4.26) |
| 6 | 26.3 (4.37) | 57.2 (5.34) |
| 7 | 36.1 (6.36) | 48.8 (3.20) |
| 11 | 35.0 (10.1) | 37.1 (4.42) |
| 12 | 18.2 (2.73) | 24.9 (10.2) |
| 13 | 16.7 (3.25) | 24.2 (5.05) |
| 17 | 27.4 (7.02) | 44.1 (3.83) |
| 18 | 27.9 (3.09) | 48.9 (9.69) |
| Indomethacin | 28.3 (4.10) | 43.6 (9.42) |

Experimental Example 2
Action on stress ulcer in mice induced by constraint under water immersion
Test Method Six-week old male ddy rats (10 rats in one group) were completely fasted overnight and then loaded with constraint under water immersion for 7 hours. The rats were observed under a stereoscopic microscope to examine production of gastric ulcer. Sum (mm) of lengths of ulcers for each animal was taken as ulcer index. Ten mg, 30 mg or 100 mg of the instant compound was mixed with 0.15 ml of Tween 80 and suspended into a 0.5% by weight aqueous solution of gum arabic to give a total 10 ml of a suspension. The suspension was orally administered 15 minutes before loading of the constraint under water immersion. Indomethacin was used as a comparative drug.

Test Results

The test results are shown in Table 3 in terms of an average value of ulcer indexes. In the respective groups given indomethacin 1 mg/kg and 3 mg/kg, the ulcer index values were 19.0 and 28.2 and there were observed increases in ulcer index as compared with the ulcer index, 9.0, obtained for the group given the solvent (which was prepared by adding 0.15 ml of Tween 80 to a 0.5% by weight aqueous solution of gum arabic so as to give a total 10 ml of a solution). In the groups given the compound of Example 1, however, no evident difference in ulcer index was observed even in the group given 100 mg/kg. This reveals that the instant compound does not show such an ulcer-exacerbating action as observed with administration of indomethacin.

TABLE 3

| Test compound (Example No.) | Ulcer index |
| --- | --- |
| Solvent-given group | 9.0 |
| Compound No. 1 | |
| 10 mg/kg | 6.5 |
| 30 mg/kg | 10.8 |
| 100 mg/kg | 9.6 |
| Indomethacin | |
| 1 mg/kg | 19.0 |
| 3 mg/kg | 28.2 |

Experimental Example 3

Action on activity of cyclooxygenase of sheep seminal vesicle gland

Test Method

Two hundred and fifty $\mu l$ of an enzyme solution containing each test compound [5 mM triptophan, 200 nM hematin, 0.04% by weight Tween 20, 10 units of cyclooxygenase of sheep seminal vesicle gland (made by CAYMAN CO., LTD.), 2 $\mu M$ [1-$^{14}$C] arachidonic acid, 0.1 M Tris-hydrochloric acid buffer solution (pH: 8.0)], underwent a reaction at 25° C. for 6 minutes. The reaction was terminated by addition of 0.5 ml of a 0.2 M citric acid buffer solution (pH 3.0). [1-$^{14}$C]arachidonic acid was extracted with ethyl acetate and separated by a thin layer chromatography. The radioactivity of the resulting arachidonic acid fraction was determined with a scintillation counter and the inhibition was calculated.

Test Results

The test results are shown in Table 4 in terms of an average value of inhibitions obtained from two experiments. The inhibition value was calculated according to the following formula:

$$\text{Inhibition (\%)} = [1 - (\text{Amount of arachidonic acid in the enzyme} - \text{unadded solution} - \text{Amount of arachidonic acid in the test compound} - \text{added solution})/(\text{Amount of arachidonic acid in the enzyme} - \text{unadded solution} - \text{Amount of arachidonic acid in the test compound} - \text{unadded solution})] \times 100$$

Indomethacin inhibited the activity of cyclooxygenase at concentrations of not lower than $10^{-8}$ M, which was dependent on dosage, and completely inhibited the activity at a concentration of $10^{-6}$ M. In contrast thereto, the compound of Example 1 did not inhibit the activity of cyclooxygenase even in $10^{-4}$ M added group.

TABLE 4

| Test (Example No.) | Inhibition (%) |
| --- | --- |
| Compound No. 1 | |
| $10^{-6}$ M | 3.4 |
| $10^{-5}$ M | 1.3 |
| $10^{-4}$ M | −2.2 |
| Indomethacin | |
| $10^{-8}$ M | 15.4 |
| $10^{-7}$ M | 66.2 |
| $10^{-6}$ M | 104.9 |

As described above, the compound of the present invention exerts an inhibitory effect on rat adjuvant arthritis and does not show an activity of inhibiting the cyclooxygenase of sheep seminal vesicle gland, which is different from conventional non-steroid anti-inflammatory agents such as indomethacin and aspirin. Further, the compound of the present invention does not show an action of exacerbating stress ulcer in mice induced by constraint under water immersion, which reveals that the compound of the present invention is an anti-inflammatory agent causing less lesion of digestive organs.

The present invention will be explained more specifically by referring to Examples.

$^1$H-NMR spectra were obtained using tetramethylsilane (TMS) as an internal standard on JNM-EX 270 spectrometer (270 MHz, made by JEOL LTD.), wherein δ values are indicated in terms of ppm. The solvent used in measuring NMR spectra was $CDCl_3$ unless otherwise noted. Mass spectra were obtained on QP 1000 EX spectrometer (made by SHIMADZU CORPORATION).

EXAMPLE 1

5-Cyano-2-(4-fluorophenyl)-3-(4-methylsulfonylphenyl) thiophene (300 mg, 0.837 mmol) was dissolved into 3 mm of dry 1,1,2,2-tetrachloroethane. To the solution was added anhydrous aluminum chloride (226 mg, 2.0 equivalents) and agitated at a room temperature for an hour. m-Chloroaniline (0.14 ml, 1.5 equivalents) was added, heated up to 100° C. and agitated for 8 hours, during which an appropriate amount of the aniline was added if the amount of the aniline was reduced. The solvent was evaporated and a saturated aqueous solution of sodium hydrogen carbonate was added to the residue, followed by extraction with chloroform. The extract was washed with water, dried and concentrated. The residue was purified by a silica gel column chromatography to give a powder (356 mg) of 5-[$N^1$-(3-chlorophenyl)amidino]-2-(4-fluorophenyl)-3-(4-methylsulfonylphenyl)thiophene.

EXAMPLES 2 TO 18

The same procedures as in Example 1 except that substituted anilines shown in Tables 5 to 8 were used were repeated to give desired compounds shown in Tables 5 to 8. The yields and instrumental analysis data are shown in Tables 5 to 18.

TABLE 5

| Ex. No. | $R^1$ | $R^2$ | Yield (%) | NMR (CDCl$_3$, δ) | Mass (m/z) | mp (° C.) |
|---|---|---|---|---|---|---|
| 1 | 3-Cl | H | 90 | 3.08(3H, s), 4.96(2H, s), 6.89(1H, dd, J=2.97, 7.92Hz), 6.99–7.09(4H, m), 7.23–7.32(3H, m), 7.43–7.48(3H, m), 7.86(2H, d, J=8.58Hz) | 484(M$^+$), 358, 277, 127 | 188.0–188.8 |
| 2 | H | H | 95 | 3.07(3H, s), 4.92(2H,.s), 6.98–7.12(5H, m), 7.23–7.28(2H, m), 7.34–7.47(5H, m), 7.85(2H, d, J=8.58Hz) | 450(M$^+$), 357, 277, 93 | 188.1–189.4 |
| 3 | 2-Cl | H | 93 | 3.08(3H, s), 4.85(2H, s), 6.99–7.07(4H, m), 7.24–7.29(3H, m), 7.42–7.47(3H, m), 7.51(1H, s), 7.86(2H, d, J=8.58Hz) | 484(M$^+$), 449, 277, 127 | 115.6–119.7 |
| 4 | 4-Cl | H | 70 | 3.23(3H, s), 6.67(2H, s), 6.88(2H, d, J=8.58Hz), 7.22(2H, t), 7.32–7.38(4H, m), 7.50(2H, d, J=8.58Hz), 7.90(2H, d, J=8.58Hz), 8.00(1H, s) DMSO-d$_6$ | 484(M$^+$), 357, 277, 127 | 245.2–298.6 (decomposed) |
| 5 | 3-F | H | 85 | 3.08(3H, s), 4.96(2H, s), 6.72–6.82(3H, m), 7.02(2H, t), 7.23–7.36(3H, m), 7.43–7.48(3H, m), 7.86(2H, d, J=8.58Hz) | 468(M$^+$), 358, 277, 111 | 108.6–112.9 |

TABLE 6

| Ex. No. | $R^1$ | $R^2$ | Yield (%) | NMR (CDCl$_3$, δ) | Mass (m/z) | mp (° C.) |
|---|---|---|---|---|---|---|
| 6 | 4-F | H | 85 | 3.08(3H, s), 4.91(2H, s), 6.93–7.10(6H, m), 7.25(2H, t), 7.43–7.46(3H, m), 7.86(2H, d, J=8.58Hz) | 468(M$^+$), 358, 279, 111 | 212.0–213.6 |
| 7 | 4-Br | H | 68 | 3.10(3H, s), 5.66(2H, s), 6.90(2H, d, J=8.58Hz), 7.03(2H, t), 7.25–7.30.(2H, m), 7.43–7.49(4H, m), 7.70(1H, s), 7.85(2H, d, J=8.58Hz) CDCl$_3$+DMSO | 530(M$^+$), 357, 277, 171 | 249.8–253.0 |
| 8 | 3-Me | H | 88 | 2.35(3H, s), 3.08(3H, s), 4.90(2H, s), 6.81(2H, d, J=8.58Hz), 6.91(1H, d, J=7.59Hz), 7.01(2H, t), 7.22–7.28(3H, m), 7.43–7.46(3H, m), 7.86(2H, d, J=8.58Hz) | 464(M$^+$), 357, 277, 107 | 104.4–106.9 |
| 9 | 4-Me | H | 78 | 2.34(3H, s), 3.08(3H, s), 4.89(2H, s), 6.90(2H, d, J=7.92Hz), 7.01(2H, t), 7.17(2H,d , J=7.92Hz), 7.25(2H, t), 7.43–7.46(3H, m), 7.86(2H, d, J=8.58Hz) | 464(M$^+$), 357, 277, 107 | 225.6–228.9 |

TABLE 7

| Ex No. | $R^1$ | $R^2$ | Yield (%) | NMR (CDCl$_3$, δ) | Mass (m/z) | mp (° C.) |
|---|---|---|---|---|---|---|
| 10 | 3-OMe | H | 70 | 3.08(3H, s), 3.81(3H, s), 4.94(2H, s), 6.57–6.67(3H, m), 7.02(2H, t), 7.23–7.30(3H, m), 7.43–7.47(3H, m), 7.86(2H, d, J=8.58Hz) | 480(M$^+$), 357, 277, 123 | 200.5–201.8 |
| 11 | 4-OMe | H | 73 | 3.08(3H, s), 3.81(3H, s), 4.90(2H, s), 6.90–7.05(6H, m), 7.25(2H, t), 7.43–7.46(3H, m), 7.86(2H, d, J=8.25 Hz) | 480(M$^+$), 357, 279, 123, 108 | 203.6–207.5 |

TABLE 7-continued

| Ex. No. | R¹ | R² | Yield (%) | NMR (CDCl$_3$, δ) | Mass (m/z) | mp (° C.) |
|---|---|---|---|---|---|---|
| 12 | 2-F | 4-F | 88 | 3.08(3H, s), 4.96(2H, s), 6.87–6.94(2H, m), 6.98–7.07(3H, m), 7.23–7.28(2H, m), 7.42–7.49(3H, m), 7.86(2H, d, J=8.58Hz) | 486(M⁺), 357, 277, 129 | 109.0–113.6 |
| 13 | 2-Cl | 4-C 1 | 83 | 3.08(3H, s), 4.88(2H, s), 6.96–7.06(3H, m), 7.22–7.29(3H, m), 7.43–7.46(3H, m), 7.51(1H, s), 7.86(2H, d, J=8.25Hz) | 518(M⁺), 483, 357, 277, 161 | 174.6–176.3 |
| 14 | 3-Me | 4-Me | 93 | 2.24(3H, s), 2.26(3H, s), 3.08(3H, s), 4.90(2H, s), 6.74–6.80(2H, m), 7.01(2H, t), 7.12(1H, d, J=7.59Hz), 7.23–7.28(2H, m), 7.43–7.46(3H, m), 7.86(2H, d, J=8.25Hz) | 478(M⁺), 357, 277, 121 | 108.7–111.4 |

TABLE 8

| Ex. No. | R¹ | R² | Yield (%) | NMR (CDCl$_3$, δ) | Mass (m/z) | mp (° C.) |
|---|---|---|---|---|---|---|
| 15 | 3-OMe | 5-OMe | 50 | 3.08(3H, s), 3.79(6H, s), 4.98(2H, s), 6.18–6.23(3H, m), 7.02(2H, t), 7.25(2H, t), 7.43–7.47(3H, m), 7.86(2H, d, J=8.58Hz) | 510(M⁺), 357, 277, 153 | 228.7–231.0 |
| 16 | 3-Cl | 4-Me | 85 | 2.35(3H, s), 3.08(3H, s), 4.92(2H, s), 6.81(1H, dd), 6.99–7.05(3H, m), 7.19–7.29(3H, m), 7.43–7.46(3H, m), 7.86(2H, d, J=8.58Hz) | 498(M⁺), 357, 278, 141, 106 | 209.9–210.8 |
| 17 | 3-Cl | 4-Cl | 98 | 3.08(3H, s), 4.97(2H, s), 6.86(1H, dd, J=2.31, 8.58Hz), 7.02(2H, t), 7.13(1H, d, J=2.31Hz), 7.25(2H, t), 7.40–7.48(4H, m), 7.86(2H, d, J=8.25Hz) | 518(M⁺), 357, 277, 161 | 116.1–119.3 |
| 18 | 3-Cl | 4-F | 98 | 3.08(3H, s), 4.97(2H, s), 6.84–6.89(1H, m), 6.99–7.17(4H, m), 7.25(2H, t), 7.42–7.47(3H, m), 7.86(2H, d, J=8.58Hz) | 502(M⁺), 358, 279, 145 | 106.1–110.2 |

Examples of formulations containing the instant compound are shown below.

Formulation Example 1

Into 200 ml of ethanol were dissolved 50 g of Compound No. 1 and 33 g of polyvinylpyrrolidone and the ethanol was distilled off under a reduced pressure. The residue was ground to a powder. To the powder were added 22 g of lactose, 21 g of carboxymethyl cellulose calcium and 1 g of magnesium stearate. The resultant was tabletted in a usual manner to give 1,000 tablets each containing 50 mg of Compound No. 1.

Formulation Example 2

A centrifugal fluidized bed granulator (CF-360, made by Freund Industry Co., Ltd.) was charged with 1,650 g of lactose (100 mesh, made by DMV CO., LTD.) and the lactose was coated in a usual manner by spraying 5,000 ml of a solution prepared by completely dissolving 50 g of Compound No. 1 and 310 g of hydroxypropyl methyl cellulose 2910 (HMPC 2910, made by Shin-Etsu Chemical Co., Ltd.) into ethanol-methylene chloride (1:1 by volume) to give granules.

The granules were dried at 40° C. for 4 hours and treated in a usual manner to give finished granules. The granules were mixed with 3 g of magnesium stearate and the resultant was charged into capsules, thereby giving 1,000 capsules each containing 50 mg of Compound No. 1.

Formulation Example 3

A centrifugal fluidized bed granulator (DF-360, Freund Industry Co., Ltd.) was charged with 1,620 g of lactose (100 mesh, made by DMV CO., LTD.) and the lactose was coated in a usual manner by spraying 1,000 ml of a solution prepared by completely dissolving 50 g of Compound No. 1 and 310 g of hydroxypropyl methyl cellulose 2910 (HMPC 2910, made by Shin-Etsu Chemical Co., Ltd.) into ethanol-methylene chloride (1:1 by volume) to give granules. The granules were dried at 40° C. for 4 hours and treated in a usual manner to give final granules.

The phenylamidinothiophene derivative of the present invention possesses anti-inflammatory activity and does not inhibit the activity of cyclooxygenase and, hence, does not show an action of exacerbating lesion of digestive organs, which are different from conventional non-steroid anti-inflammatory agents. Accordingly, the derivative can be an anti-inflammatory agent which is useful for prevention and treatment of various inflammatory diseases and shows less side effect.

We claim:

1. A thiophene derivative containing a phenylamidino group represented by the general formula (I):

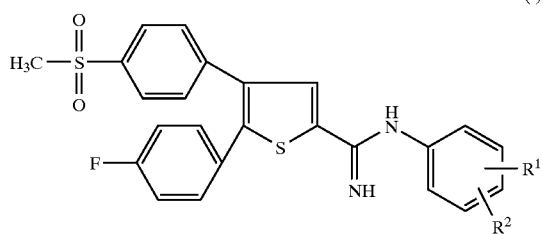

(I)

wherein $R^1$ and $R^2$ are the same or different from each other and are hydrogen atom, a halogen atom, an alkyl group having 1 to 4 carbon atoms or an alkoxyl group having 1 to 4 carbon atoms; or a pharmacologically acceptable salt thereof.

2. The thiophene derivative containing a phenylamidino group or a pharmacologically acceptable salt thereof according to claim 1, wherein $R^1$ and $R^2$ in the general formula (I) are the same or different from each other and are hydrogen atom, fluorine atom, chlorine atom, bromine atom, methyl group or methoxy group.

3. 5-[$N^1$-(3-chlorophenyl)aminido]-2-(4-fluorophenyl)-3-(4-methylsulfonylphenyl)thiophene or a pharmacologically acceptable salt thereof.

4. An anti-inflammatory agent containing a thiophene derivative containing a phenylamidino group set forth in any of claims 1 to 3, or a pharmacologically acceptable salt thereof.

5. A method of treating an inflammatory disease in a patient which comprises administering to the patient a therapeutically effective amount of a thiophene derivative of formula (I) as set forth in any of claims 1 to 3, or a pharmacologically effective salt thereof.

* * * * *